(12) United States Patent
Buxton et al.

(10) Patent No.: US 11,318,247 B2
(45) Date of Patent: May 3, 2022

(54) LOW FLOW INFUSION PUMP STARTUP

(71) Applicant: B. Braun Medical Inc., Bethlehem, PA (US)

(72) Inventors: Sean Buxton, Providence, RI (US); Benjamin Vespone, North Providence, RI (US)

(73) Assignee: B Braun Medical Inc., Bethlehem, PA (US)

( * ) Notice: Subject to any disclaimer, the term of this patent is extended or adjusted under 35 U.S.C. 154(b) by 197 days.

(21) Appl. No.: 16/705,629

(22) Filed: Dec. 6, 2019

(65) Prior Publication Data
US 2021/0170096 A1     Jun. 10, 2021

(51) Int. Cl.
*A61M 5/142* (2006.01)
*A61M 5/145* (2006.01)

(52) U.S. Cl.
CPC .......... *A61M 5/14228* (2013.01); *A61M 2005/14208* (2013.01); *A61M 2005/14533* (2013.01); *A61M 2205/3334* (2013.01)

(58) Field of Classification Search
CPC .... A61M 5/14228; A61M 2005/14533; A61M 2005/14208; A61M 2205/3334; A61M 5/142; A61M 2205/12; A61M 2205/121; F04B 43/08; F04B 43/082; F04B 43/12; F04B 43/1215; F04B 43/1223
See application file for complete search history.

(56) References Cited

U.S. PATENT DOCUMENTS 5,279,556 A  *  1/1994  Goi et al. .......... A61M 5/14212
                                                      604/67

* cited by examiner

*Primary Examiner* — Kami A Bosworth
*Assistant Examiner* — Emily J Becker

(57) ABSTRACT

A peristaltic infusion pump with improved low flow performance. The pump includes a cam shaft having cams offset in an axial direction, pump fingers that engage a tube, each finger coupled to a respective cam, the fingers creating a pumping region and an occlusion region within the tube, a motor coupled to the cam shaft, a memory, and a controller. The controller implements cam rotation instructions received from the memory to cause the pump to position the fingers in the occlusion region prior to beginning an infusion therapy to deliver fluid to patient through the tube at a patient fluid delivery rate, rotate the cam shaft to transition the fingers from the occlusion region to the pumping region at a startup rate that is faster than a patient fluid delivery rate, and rotate the cam shaft at the patient fluid delivery rate in the pumping region.

20 Claims, 9 Drawing Sheets

LOW FLOW INFUSION PUMP STARTUP

FIELD OF THE INVENTION

The present disclosure is related to infusion pumps and, more particularly, to a startup routine for an infusion pump having improved low flow characteristics.

BACKGROUND

Infusion pumps deliver controlled doses of fluids such as medications, analgesics, and nutrition to patients. Infusion pumps are particularly well suited to delivering controlled doses of fluids over long periods of time, e.g., several hours or days. While many infusion pumps are designed for bedside use, there are ambulatory versions available. Ambulatory infusion pumps allow a patient to move around while the infusion pump is in use.

Syringe pumps and peristaltic pumps are two conventional types of infusion pumps. A syringe pump depresses a cylinder within a syringe to deliver fluid from the syringe to a patient. A peristaltic pump acts on a tube to control the rate of fluid flow through the tube from a bottle or bag of fluid to a patient. Precise delivery of fluids is desirable to optimize treatment of a patient as there are many fluids where small variations can be critical. It can be difficult to achieve precise delivery of fluids at low flow rates with peristaltic pumps.

SUMMARY

Examples described herein are directed to methods and peristaltic infusion pumps for delivering fluids to a patient. The peristaltic infusion pump includes a cam shaft having a plurality of cams offset from one another in an axial direction, a plurality of pump fingers configured to engage a tube received by the peristaltic infusion pump, each pump finger coupled to a respective one of the plurality of cams, the plurality of pump fingers creating a pumping region and an occlusion region within the received tube, a motor coupled to the cam shaft, the motor configured to rotate the cam shaft, a memory, a controller coupled to the memory and the motor. The controller implements cam rotation instructions received from the memory to cause the peristaltic infusion pump to position the plurality of pump fingers in the occlusion region prior to beginning an infusion therapy to deliver fluid to patient through the tube at a patient fluid delivery rate, rotate the cam shaft to transition the plurality of pump fingers from the occlusion region to the pumping region at a startup rate that is faster than a patient fluid delivery rate, and rotate the cam shaft at the patient fluid delivery rate in the pumping region.

DRAWINGS

The drawing figures depict multiple views of one or more implementations, by way of example only, not by way of limitations. In the figures, like reference numerals refer to the same or similar elements. The same numeral is used to represent the same or similar element across the multiple views. If multiple elements of the same or similar type are present, a letter may be used to distinguish between the multiple elements. When the multiple elements are referred to collectively or a non-specific one of the multiple elements is being referenced, the letter designation may be dropped.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and circuitry have been described at a relatively high-level, without detail, in order to avoid unnecessarily obscuring aspects of the present teachings.

Figure 1:
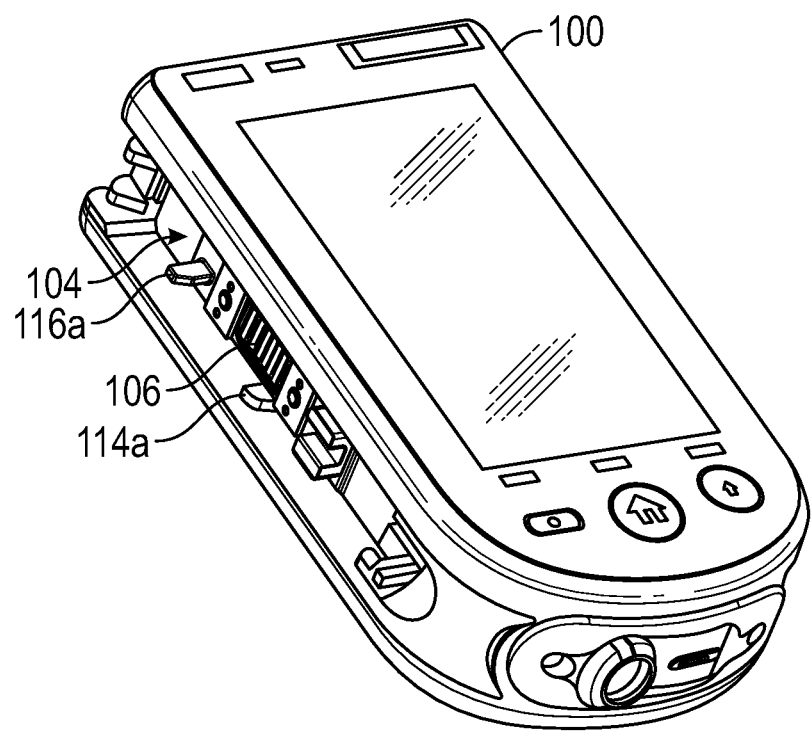
FIG. 1 is a perspective view of an example ambulatory infusion pump.
Figure 2:
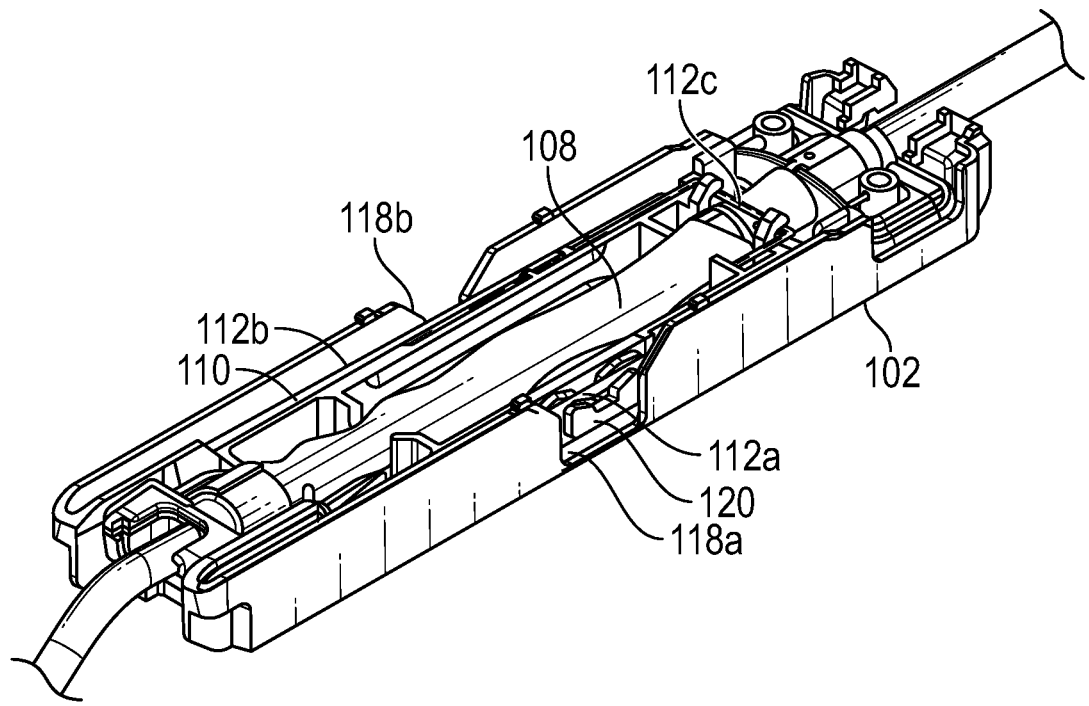
FIG. 2 is a perspective view of an example cassette with a free flow prevention clam for use with the ambulatory pump of FIG. 1.

FIG. 1 depicts an example ambulatory pump 100 and FIG. 2 depicts an example cassette 102 for use with the ambulatory pump 100. The ambulatory pump 100 includes a receptacle 104 configured to receive the cassette 102. A peristaltic pump 106 within the receptacle 104 acts upon a tube 108 extending through a channel within the cassette 102 to pump fluid from a fluid container (e.g., a bag or a bottle; not shown) into a patient. An example free flow prevention clamp 110 is positioned within the cassette 102 to allow fluid flow through the tube 108 when the cassette is coupled to the ambulatory pump 100 within the receptacle 104 (during which time the peristaltic pump 106 controls fluid flow through the tube 108) and to selectively cut off fluid flow through the tube 108 when the cassette 102 is not coupled to the ambulatory pump 100 in order to prevent unintentional fluid flow through the tube (e.g., free flow).

The ambulatory pump 100 includes a user interface for interacting with the ambulatory pump 100. The illustrated user interface includes a display (which may be a touchscreen) and buttons. A user controls operation of the ambulatory pump 100 via the user interface. The pump 100 additionally includes a housing for containing and supporting the components of the ambulatory pump 100 such as the peristaltic pump 106, electronics, and power supplies.

The free flow prevention clamp 110 includes a first elongate section 112a, a second elongate section 112b, and a clamping section 112c. The housing of the cassette 102 supports the free flow prevention clamp 110. The clamping section 112 is positioned within the cassette geometry such that, when the cassette 102 is received within the receptacle 104 of the ambulatory pump 100, the clamping section 112c extends across the channel receiving the tube 108. The housing of the cassette 102 may be rigid plastic or other material capable of supporting the tube 108 and free flow prevention clamp 110.

The ambulatory pump 100 also includes a pair of arc cams (a first arc cam 114a on one side of the receptacle is illustrated FIG. 1, with the second hidden from view) for engaging the elongate sections 112a, b of the free flow prevention clamp in order to lift the clamping section 112c. Additionally, the ambulatory pump 100 includes a pair of wedge cams (a first wedge cam 116a on one side of the receptacle 104 is illustrated FIG. 1, with the second hidden from view) for transitioning the free flow prevention clamp 110 from an open, manufactured/shipped state to an operational state, which is described in further detail below.

The cassette 102 also includes a first cutout 118a in a sidewall of the cassette 102 and a second cutout 118b in an opposite sidewall of the cassette 102. Additionally, the cassette 102 includes a touch pad 120 positioned on the first elongate section 112a adjacent a mid-point of the first elongate section 112a and the first cutout 118a. The touch pad 120 and cutout 118a facilitates engagement of the first elongate section 112a by a finger of an operator in order to manually lift the clamping section 112c to allow fluid flow through the tube 108 (e.g., for priming the cassette 102) when the cassette 102 is not received within the receptacle 104 of the ambulatory pump 100. The touch pad 120 may be a press fit piece of rigid plastic. Although the touch pad 120 is illustrated as only on the first elongate section 112a, a touch pad may also be provided on the second elongate section 112b.

Figure 3:
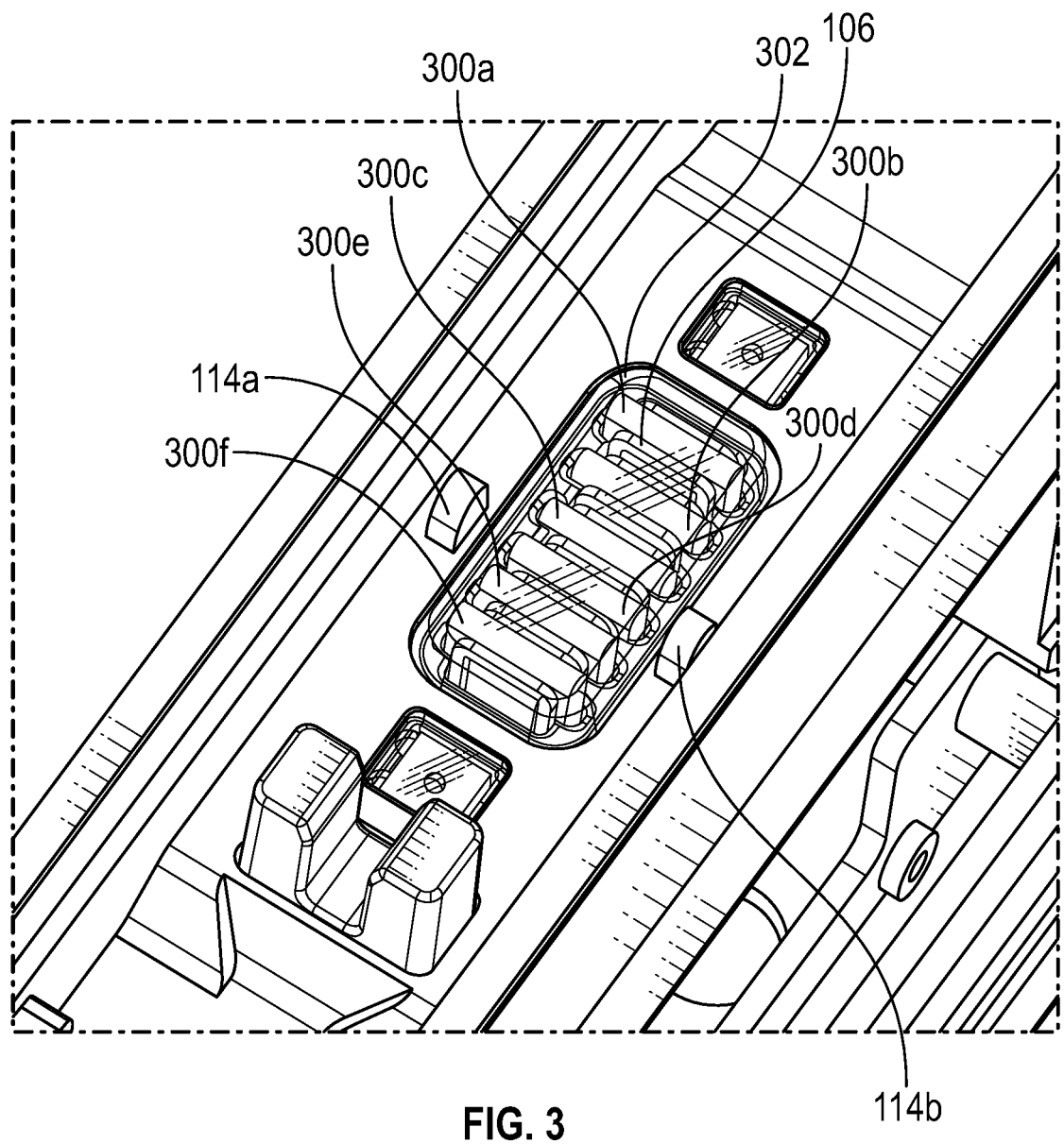
FIG. 3 is a partial perspective view of the pump of FIG. 1A illustrating cams that engage the free flow prevention clamp when the cassette is coupled to the pump.

FIG. 3 depicts the arc cams 114 and peristaltic pump 106 of the ambulatory pump 100. The peristaltic pump 106 includes multiple pump fingers 300 (six pump fingers 300a-f illustrated in FIG. 3). A flexible barrier 302 separates the pump fingers 300 (and other pump components of a pumping mechanism) from the receptacle area 104 receiving the cassette 102 with the tube 108. The flexible barrier 302 provides a barrier between the fluid delivery apparatus/cassette and the pumping mechanism to prevent fluid from damaging components of the pumping mechanism.

Figure 4:
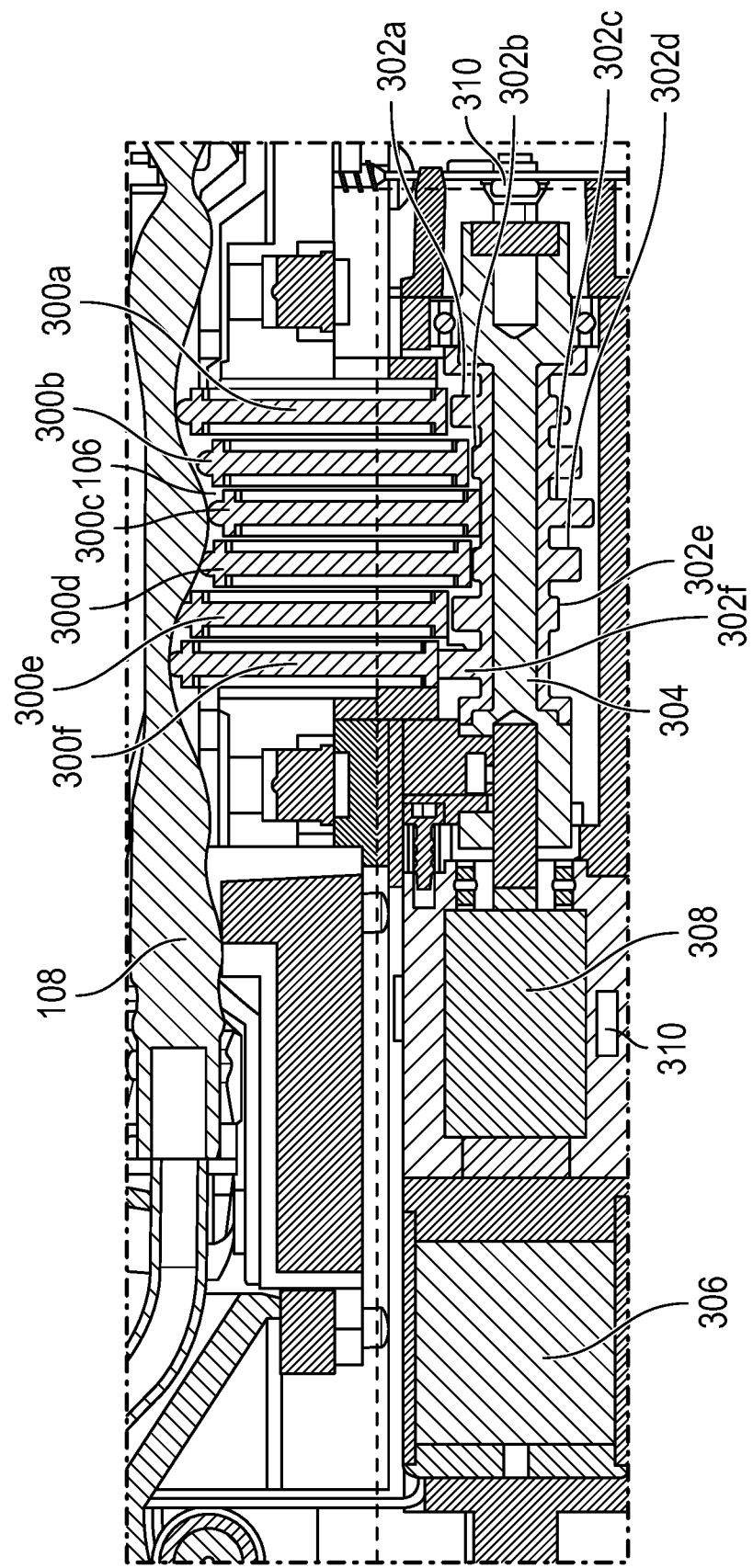
FIGS. 4 and 5 are cutaway views of the pump illustrating pump fingers and cams for moving the pump fingers of the ambulatory pump of FIG. 1.
Figure 5:
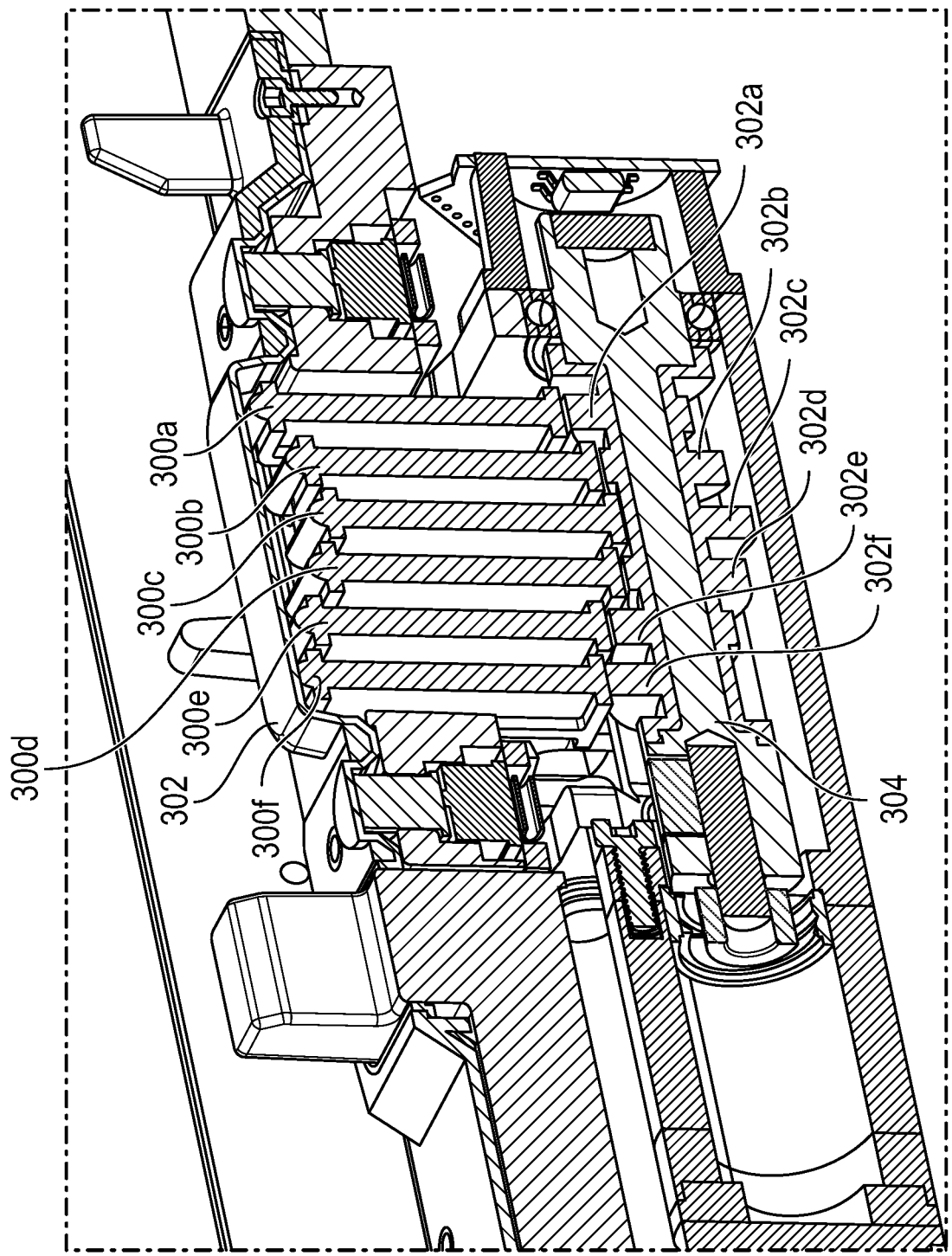

FIGS. 4 and 5 are cutaway views of the ambulatory pump 100. Multiple cams 302 (six cams 302a-f) supported by a cam shaft 304 act on respective pump fingers 300. The cams 302 raise and lower the pump fingers 300, which engage the tube 108 of the cassette 102 in order to force fluid though the tube 108. A motor 306 under control of a controller 310 turns the cam shaft 304 by way of a gearbox 308. As the cam shaft 304 turns, the cams 302, which are offset from each other in an axial direction, raise and lower respective pump fingers 300. For example, cam 302a raises and lowers pump finger 300a. Controller 310 may be an standalone or embedded processor configured to carry out instructions in order to control operations of the ambulatory pump 100.

Figure 6:
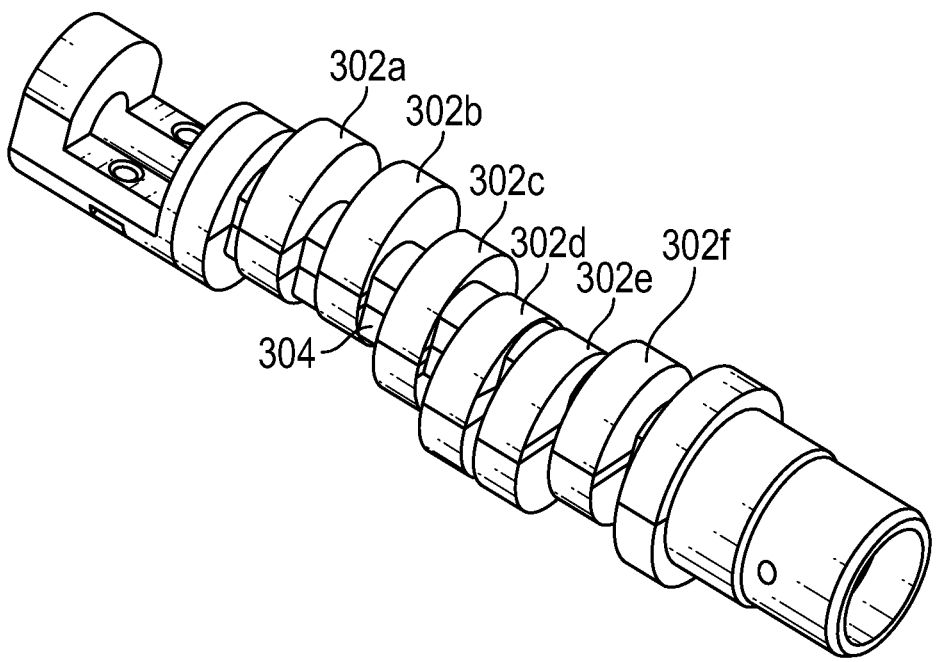
FIG. 6 is a perspective view of the cams on a cam shaft of the ambulatory pump of FIG. 1.
Figure 7:
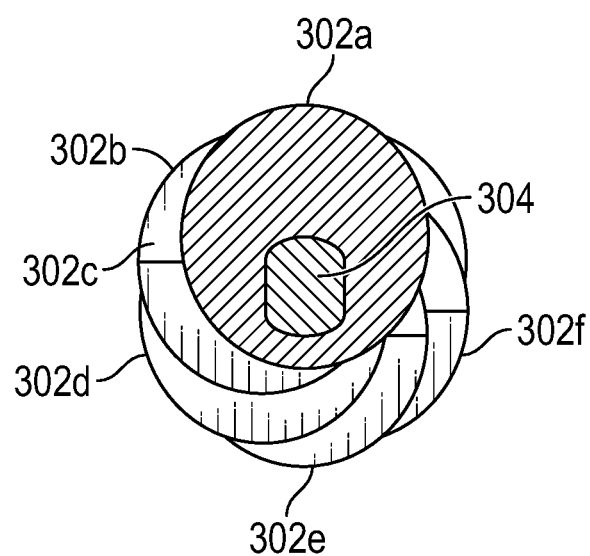
FIG. 7 is a schematic end view of the cams on the cam shaft depicting their offset in an axial direction.

FIG. 6 depicts the cam shaft 304 with cams 302 offset from one another along the length of the cam shaft 304. FIG. 7 schematically illustrates the offset cams 302 positioned on the cam shaft 304. Each of the illustrated cams 304 are circular in shape. The center of each cam 302 is offset with respect to the cam shaft 304 extending through the cams. In an example, each cam 302 is eight (8) millimeters in diameter and the cam shaft 304 passes through each cam 302 at a point that is 2.5 millimeters from one edge and 5.5 millimeters from the opposite edge along a line bisecting the cam 302. Rotation of a cam 302 about the cam shaft 304 will raise and lower a respective pump finger 304 three (3) millimeters. In the illustrated example, the six cam 302a-f are uniformly distributed around the cam shaft 304 in a direction extending through a longitudinal axis of the cam shaft 304.

Figure 8:
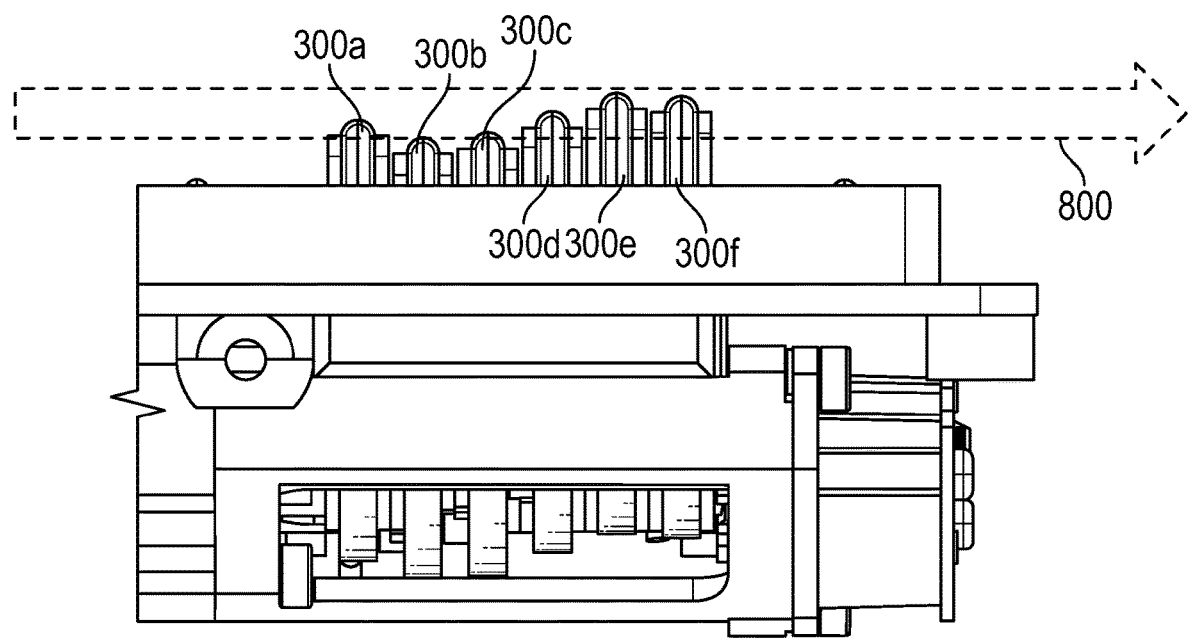
FIG. 8 is a side view of the peristaltic pump within the ambulatory infusion pump with the pump fingers of the ambulatory infusion pump in an occluded region of a fluid delivery cycle.
Figure 9:
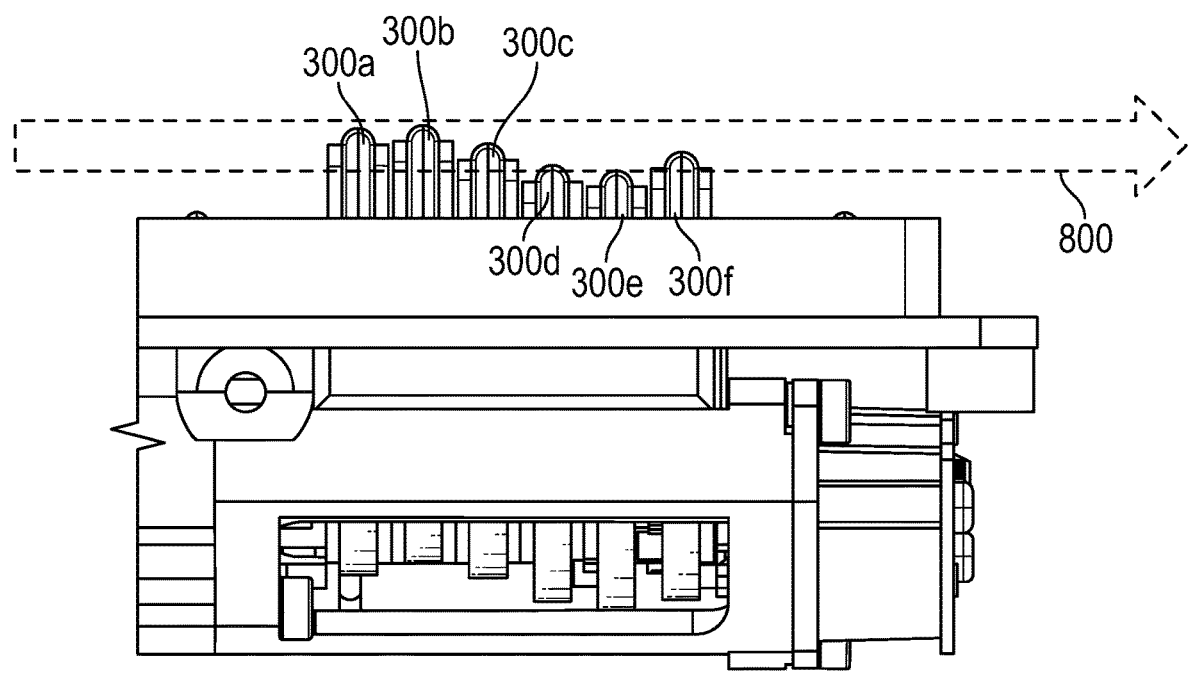
FIG. 9 is a side view of the peristaltic pump within the ambulatory infusion pump with the pump fingers of the ambulatory infusion pump in a pumping region of the fluid delivery cycle.

FIG. 8 is a side view of the peristaltic pump 106 within the ambulatory infusion pump 100 with the pump fingers 300 of the ambulatory infusion pump 100 in an occluded region of a fluid delivery cycle with respect to a fluid deliver direction 800 through the tube 108. As seen in FIG. 8, pump fingers 300e and 300f are raised, effectively preventing any further ability for the peristaltic pump 106 to force fluid through the tube 108 toward the patient. This is referred to herein as an occlusion region FIG. 9 is a side view of the peristaltic pump 106 within the ambulatory infusion pump 100 with the pump fingers 300 of the ambulatory infusion pump 100 in a pumping region of a fluid delivery cycle with respect to a fluid deliver direction 800 through the tube 108. As seen in FIG. 9, pump finger 300d, e, and f are lowered, effectively allowing fingers 300b, c of the peristaltic pump 106 to force fluid through the tube 108 toward the patient. This is referred to herein as a pumping region.

Figure 10:
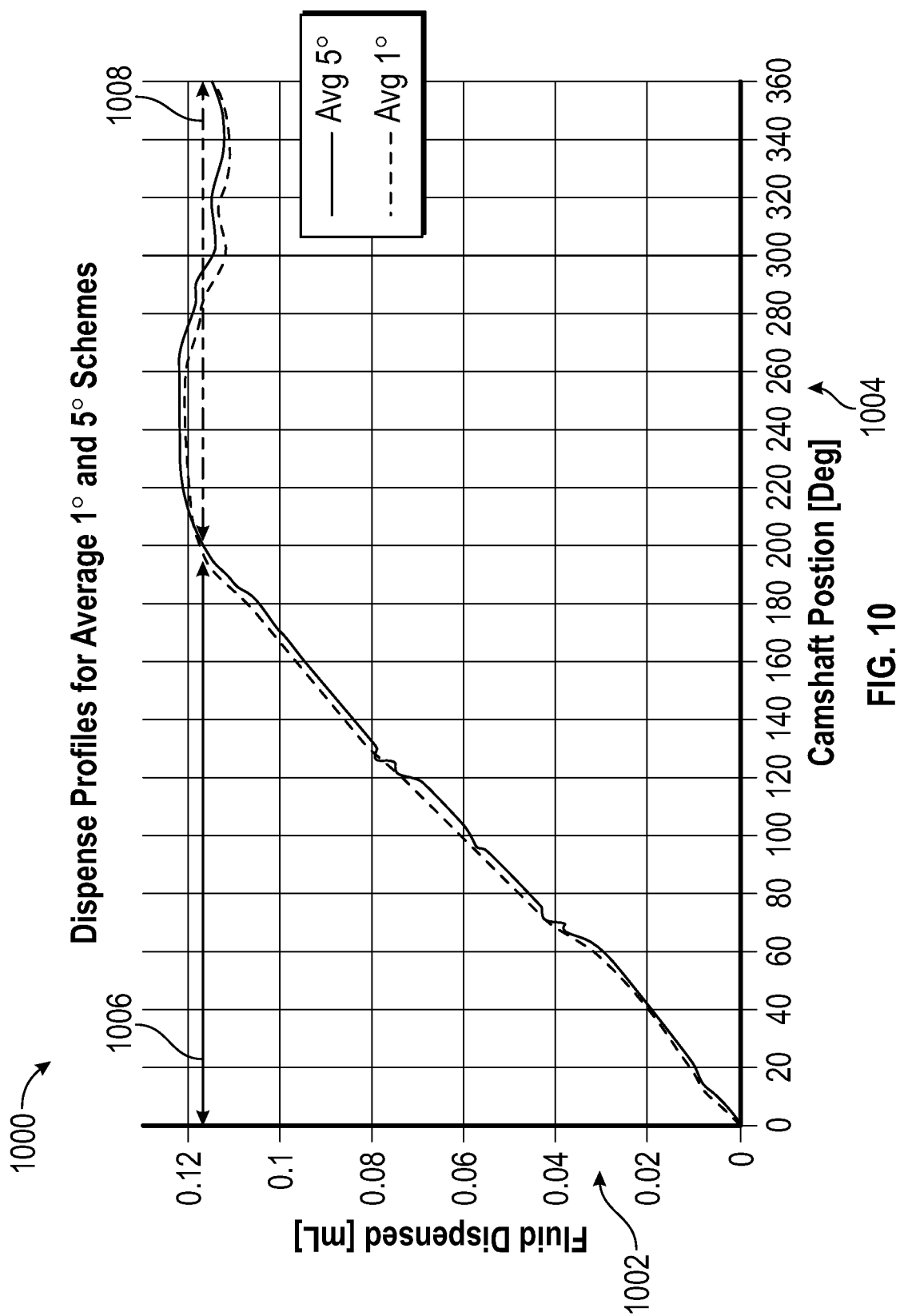
FIG. 10 is a graph depicting an amount of fluid dispensed versus cam shaft position for the ambulatory pump of FIG. 1.

FIG. 10 is a graph depicting an amount of fluid dispensed 1002 versus cam shaft position 1004 for the ambulatory pump 100 of FIG. 1. As depicted, between a cam shaft position 1004 of 0 degrees and 200 degrees, the peristaltic pump 106 is in a pumping region 1006. During the remaining 160 degrees of a full rotation, the peristaltic pump 106 is in an occlusion region. FIG. 10 depicts a relatively uniform fluid delivery profile in the pumping region 1006 and a relatively flat fluid delivery profile (indicating no/low fluid flow) during the occlusion region 1008. The fluid delivery profiles are for a cam rotation in 1 degree increments (dashed line) and 5 degree increments (solid line).

Figure 11:
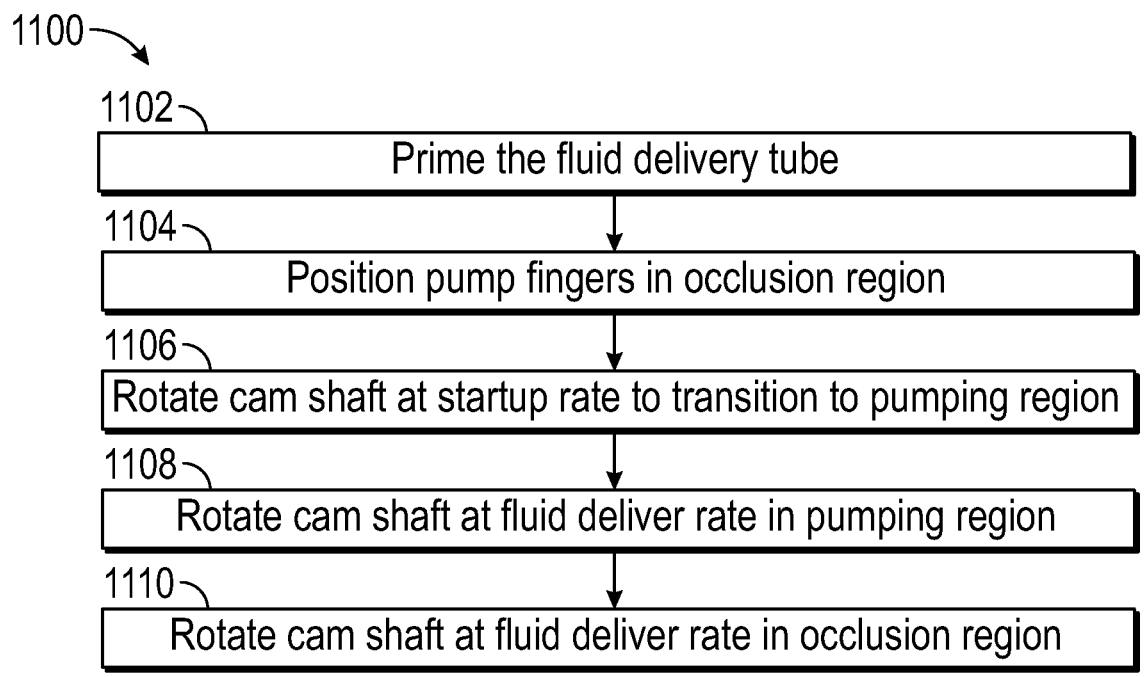
FIG. 11 is a flow chart depicting a startup routine for use with the ambulatory pump of FIG. 1.

FIG. 11 is a flow chart depicting a startup routine for use with the ambulatory pump of FIG. 1. The steps are described with reference to hardware described herein but are not to be limited to such implementations. One of skill in the art will understand from the description herein that one or more steps/blocks may be omitted, and one or more additional/alternative steps may be incorporated.

At block 1102, prime the fluid delivery tube 1102 to make it ready to deliver fluid to the patient. In an example, the peristaltic pump 106 is used to prime the fluid delivery tube 108 by pumping fluid through the tube 108 until it beings to flow at a patient end of the tube. In another example, the fluid delivery tube 108 is manually (i.e., gravity) primed.

At block 1104, position pump finger in an occlusion region. The peristaltic pump 106 may be positioned by a controller 310 in an occlusion region 1008 such as depicted in FIG. 10. In an example, the pump fingers 300 of the peristaltic pump 106 are positioned at the beginning of the occlusion region (e.g., at a cam shaft position of 200 degree; see FIGS. 8 and 10).

At block 1106, rotate the cam shaft at a startup rate to transition from the occlusion region to the beginning of the pumping region. A controller 310 causes the cam shaft 306 to rotate at a relatively rapid rate (e.g., 1.5 times the patient fluid delivery rate). The cam shaft 306 of the peristaltic pump 106 is rotated until it transitions to the pumping 1006 such as depicted in FIG. 10. In an example, the cam shaft is rotated at the startup rate until the pump fingers 300 of the peristaltic pump 106 are positioned at the beginning of the pumping region (e.g., at a cam shaft position of 0 degree; see FIGS. 9 and 10).

At block 1108, rotate the cam shaft at a patient fluid delivery rate in the pumping region 1006 during a patient fluid delivery therapy. A controller 310 causes the cam shaft 306 to rotate at the patient fluid delivery rate during the patient fluid delivery therapy.

At block 1110, rotate the cam shaft at the patient fluid delivery rate in the occlusion region 1008 during the patient fluid delivery therapy. In an example, a controller 310 causes the cam shaft 306 to rotate at the same rate during the occlusion region 1008 as during the pumping region 1006 for the remainder of the patient fluid delivery therapy.

Peristaltic pumps create flow by occluding a tube or other flexible membrane to create flow. Without being limited to a particular theory, the inventors discovered that there is some wasted motion due to the occlusion interface where no fluid is trapped behind the occlusion of the tube. The occlusion forms distinct areas in the fluid delivery profile where no fluid is delivered. There is distinct regions of fluid delivery and regions where the pump is no longer delivering fluid for a given pump rotation. For continuous pump cam shaft rotation, it creates pauses in the fluid movement in the tube.

This limitation of the peristaltic mechanism is used advantageously in low flow control using the methods and pumps described herein. Low flow control of the infusion pump (0.1 ml/hr to 1 ml/hr) becomes difficult due to many outside factors. One characteristic of infusion pumps is the time for an infusion to start. At low flow rates the startup time is increased due to smaller pressures generated due to slow speeds of the pump camshaft. The methods and pumps described herein compensate for the compliance of the downstream tubing. The infusion pump essentially inflates the downstream tubing with volume to overcome the compliance of the tubing and create a pressure gradient to deliver fluid to the patient. At low flow rates, the pump is limited by the rate it can increase the pressure in the tubing due to the slow cam shaft speeds.

Intuitively, it would make sense to begin the low flow infusion at the beginning of the pumping region of the peristaltic mechanism. The issue with this, however, is that it exposes the largest region of complaint tubing. Due to the increased compliance, there is more volume needed to inflate the tubing to create flow. This increased volume leads to increased start up time which is un-desirable clinically.

The methods and pumps described herein compensates for this start up delay by starting during the beginning of the occlusion region of the peristaltic mechanism. This helps limit the compliance of the downstream tubing. Using this compensation allows the infusion to almost start up instantly if the line has been primed correctly. Without this method, it can delay infusions from 15 min to over an hour at low flow rates of 0.1 mL/hr.

Figure 12:
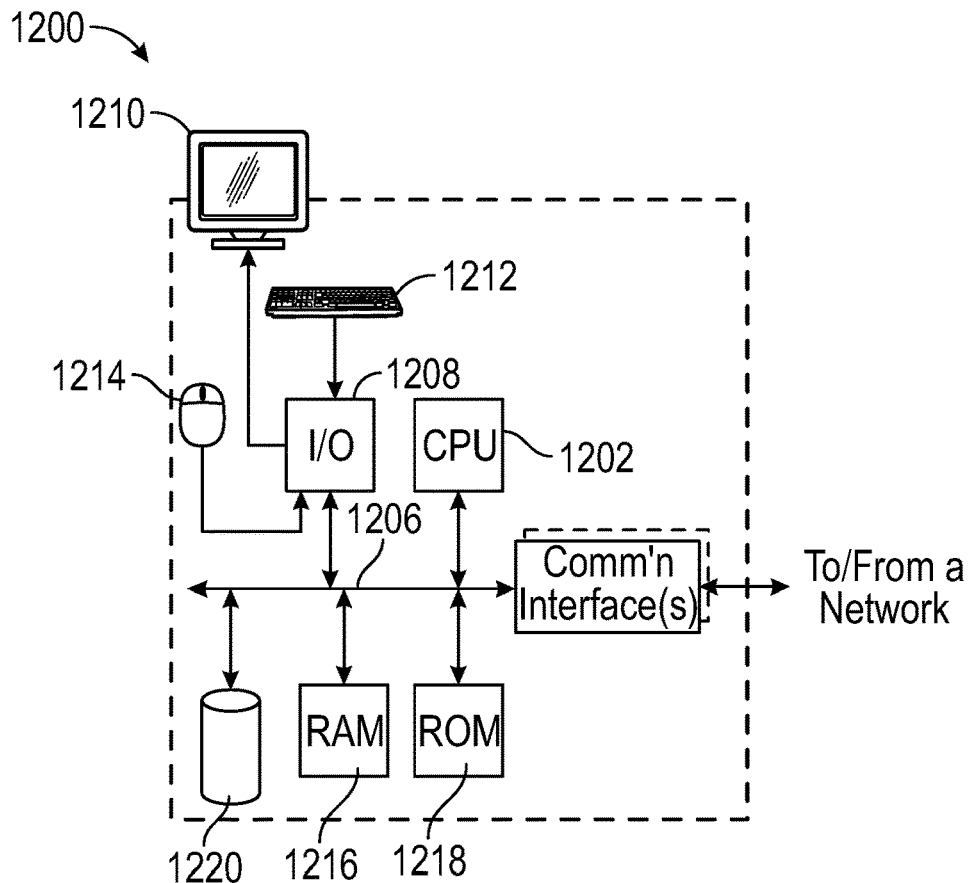
FIG. 12 is a functional block diagram illustrating a general-purpose computer hardware platform configured to implement the functional examples described with respect to FIGS. 1-11.
Figure 13:
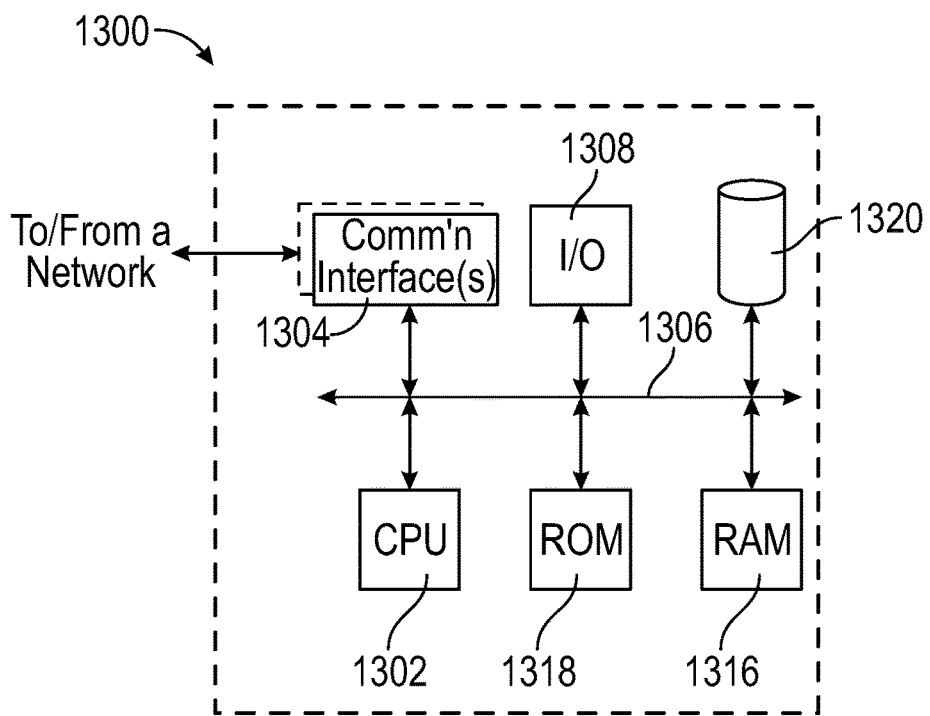
FIG. 13 is another functional block diagram illustrating a general-purpose computer hardware platform configured to implement the functional examples described with respect to FIGS. 1-11.

FIGS. 12 and 13 are functional block diagrams illustrating general-purpose computer hardware platforms configured to implement the functional examples described with respect to FIGS. 1-11 as discussed above.

Specifically, FIG. 12 illustrates an example computer platform 1200 and FIG. 13 depicts an example computer 1300 with user interface elements, as may be used to implement in a personal computer, pump 100, or other type of work station or terminal device. It is believed that those skilled in the art are familiar with the structure, programming and general operation of such computer equipment and as a result the drawings should be self-explanatory.

Hardware of an example computer (FIG. 12) includes a data communication interface for packet data communication. The server computer also includes a central processing unit (CPU) 1202, in the form of circuitry forming one or more processors, for executing program instructions. The server platform hardware typically includes an internal communication bus 1206, program and/or data storage 1216, 1218, and 1220 for various programs and data files to be processed and/or communicated by the server computer, although the server computer often receives programming and data via network communications. In one example, as shown in FIG. 12, the computer system includes a video display unit 1210, (e.g., a liquid crystal display (LCD) or a cathode ray tube (CRT)), an alphanumeric input device 1212 (e.g. a keyboard), a cursor control device 1214 (e.g. a mouse), each of which communicate via an input/output device (I/O) 1208. The hardware elements, operating systems and programming languages of such server computers are conventional in nature, and it is presumed that those skilled in the art are adequately familiar therewith. Of course, the server functions may be implemented in a distributed fashion on a number of similar hardware platforms, to distribute the processing load.

Hardware of a computer type user terminal device, such as a PC or tablet computer, similarly includes a data communication interface 1304, CPU 1302, main memory 1316 and 1318, one or more mass storage devices 1320 for storing user data and the various executable programs, an internal communication bus 1306, and an input/output device (I/O) 1308 (see FIG. 13).

Aspects of the methods for pump control, as outlined above, may be embodied in programming in general purpose computer hardware platforms (such as described above with respect to FIGS. 12 and 13), e.g. in the form of software, firmware, or microcode executable by a networked computer system such as a server or gateway, and/or a programmable nodal device. Program aspects of the technology may be thought of as "products" or "articles of manufacture" typically in the form of executable code and/or associated data that is carried on or embodied in a type of machine readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software, from one computer or processor into another, for example, from a processor 108 of the system 100 and/or from a controller 310 of a pump 100 to a computer or software of another system (not shown). Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to one or more of "non-transitory," "tangible" or "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-transitory storage media include, for example, optical or magnetic disks, such as any of the storage devices in any computer(s) or the like. It may also include storage media such as dynamic memory, for example, the main memory of a machine or computer platform. Tangible transmission media include coaxial cables; copper wire and fiber optics, including the wires that include a bus within a computer system. Carrier-wave transmission media can take the form of electric or electromagnetic signals, or acoustic or light waves such as those generated during radio frequency (RF) and light-based data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

Program instructions may include a software or firmware implementation encoded in any desired language. Programming instructions, when embodied in machine readable medium accessible to a processor of a computer system or device, render computer system or device into a special-purpose machine that is customized to perform the operations specified in the program performed by the controller 310 of the pump 100.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is ordinary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 105 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that includes a list of elements does not include only those elements but may include other elements not expressly listed or inherent to such process, method, article, or apparatus. An element preceded by "a" or "an" does not, without further constraints, preclude the existence of additional identical elements in the process, method, article, or apparatus that includes the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as a separately claimed subject matter.

While the foregoing describes what is considered to be the best mode and other examples, it is understood that various modifications may be made and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. A peristaltic infusion pump, the peristaltic infusion pump comprising:
 a cam shaft having a plurality of cams offset from one another in an axial direction;
 a plurality of pump fingers configured to engage a tube received by the peristaltic infusion pump, each pump finger coupled to a respective one of the plurality of cams, the plurality of pump fingers creating a pumping region and an occlusion region within the received tube;
a motor coupled to the cam shaft, the motor configured to rotate the cam shaft;
a memory,
a controller coupled to the memory and the motor; and
cam rotation instructions in the memory, wherein the controller is configured to receive the cam rotation instructions from the memory and execute the received cam rotation instructions and wherein execution of the cam rotation instructions by the controller configures the peristaltic infusion pump to:
position the plurality of pump fingers in the occlusion region of a fluid delivery cycle of the peristaltic infusion pump prior to a beginning of an infusion therapy to deliver fluid to a patient through the tube at a patient fluid delivery rate, the occlusion region of the fluid delivery cycle preventing the peristaltic infusion pump from forcing fluid through the tube toward the patient;
rotate the cam shaft to transition the plurality of pump fingers from the occlusion region to the pumping region prior to the beginning of the infusion therapy at a startup rate that is faster than the patient fluid delivery rate, the pumping region enabling the peristaltic infusion pump to force fluid through the tube toward the patient; and
rotate the cam shaft at the patient fluid delivery rate in the pumping region during the infusion therapy.

2. The peristaltic infusion pump of claim 1, wherein the execution of the cam rotation instructions by the controller further configures the peristaltic infusion pump to:
prime the tube before positioning the plurality of pump fingers in the occlusion region prior to beginning the infusion therapy to deliver the fluid to the patient.

3. The peristaltic infusion pump of claim 1, wherein the execution of the cam rotation instructions by the controller further configures the peristaltic infusion pump to:
rotate the cam shaft at the patient fluid delivery rate in the occlusion region after rotating the cam shaft at the patient fluid delivery rate in the pumping region.

4. The peristaltic infusion pump of claim 1, wherein the cam rotation instructions to position the plurality of pump fingers in the occlusion region prior to beginning the infusion therapy position the plurality of pump fingers at a beginning of the occlusion region.

5. The peristaltic infusion pump of claim 4, wherein the cam rotation instructions to rotate the cam shaft to transition the plurality of pump fingers from the occlusion region to the pumping region rotate the cam shaft 160 degrees at the startup rate.

6. The peristaltic infusion pump of claim 5, wherein the patient fluid delivery rate is from 0.1 milliliters per hour to 1 milliliter per hour.

7. The peristaltic infusion pump of claim 6, wherein the cam shaft is rotated in one degree increments.

8. A method for delivering fluid through a tube with a peristaltic infusion pump, the peristaltic infusion pump including a plurality of pump fingers configured to engage the tube and positioned on a cam shaft, the method comprising:
positioning the plurality of pump fingers in an occlusion region of a fluid delivery cycle of the peristaltic infusion pump prior to a beginning of an infusion therapy to deliver fluid to a patient through the tube at a patient fluid delivery rate, the occlusion region of the fluid delivery cycle preventing the peristaltic infusion pump from forcing fluid through the tube toward the patient;
rotating the cam shaft to transition the plurality of pump fingers from the occlusion region to a pumping region prior to the beginning of the infusion therapy at a startup rate that is faster than the patient fluid delivery rate, the pumping region enabling the peristaltic infusion pump to force fluid through the tube toward the patient; and
rotating the cam shaft at the patient fluid delivery rate in the pumping region during the infusion therapy.

9. The method of claim 8, further comprising:
priming the tube before positioning the plurality of pump fingers in the occlusion region prior to beginning the infusion therapy to deliver the fluid to the patient.

10. The method of claim 8, further comprising:
rotating the cam shaft at the patient fluid delivery rate in the occlusion region after rotating the cam shaft at the patient fluid delivery rate in the pumping region.

11. The method of claim 8, wherein the positioning the plurality of pump fingers in the occlusion region prior to beginning the infusion therapy comprises positioning the plurality of pump fingers at a beginning of the occlusion region.

12. The method of claim 11, wherein the rotating the cam shaft to transition the plurality of pump fingers from the occlusion region to the pumping region comprises rotating the cam shaft 160 degrees at the startup rate.

13. The method of claim 12, wherein the patient fluid delivery rate is from 0.1 milliliters per hour to 1 milliliter per hour.

14. The method of claim 13, wherein the rotating the cam shaft at the patient fluid delivery rate comprises rotating the cam shaft in one degree increments.

15. A non-transitory controller-readable storage medium storing controller-executable instructions that, when executed by a controller of a peristaltic infusion pump including a plurality of pump fingers configured to engage a tube and positioned on a cam shaft, cause the peristaltic infusion pump to perform operations comprising:
positioning the plurality of pump fingers in an occlusion region of a fluid delivery cycle of the peristaltic infusion pump prior to a beginning of an infusion therapy to deliver fluid to a patient through the tube at a patient fluid delivery rate, the occlusion region of the fluid delivery cycle preventing the peristaltic infusion pump from forcing fluid through the tube toward the patient;
rotating the cam shaft to transition the plurality of pump fingers from the occlusion region to a pumping region prior to the beginning of the infusion therapy at a startup rate that is faster than the patient fluid delivery rate, the pumping region enabling the peristaltic infusion pump to force fluid through the tube toward the patient; and
rotating the cam shaft at the patient fluid delivery rate in the pumping region during the infusion therapy.

16. The non-transitory controller-readable storage medium of claim 15, wherein the instructions further cause the peristaltic infusion pump to perform operations comprising:
priming the tube before positioning the plurality of pump fingers in the occlusion region prior to beginning the infusion therapy to deliver the fluid to the patient.

17. The non-transitory controller-readable storage medium of claim 15, wherein the instructions further cause the peristaltic infusion pump to perform operations comprising:
   rotating the cam shaft at the patient fluid delivery rate in the occlusion region after rotating the cam shaft at the patient fluid delivery rate in the pumping region.

18. The non-transitory controller-readable storage medium of claim 15, wherein the positioning the plurality of pump fingers in the occlusion region prior to beginning the infusion therapy comprises positioning the plurality of pump fingers at a beginning of the occlusion region.

19. The non-transitory controller-readable storage medium of claim 18, wherein the rotating the cam shaft to transition the plurality of pump fingers from the occlusion region to the pumping region comprises rotating the cam shaft 160 degrees at the startup rate.

20. The non-transitory controller-readable storage medium of claim 19, wherein the patient fluid delivery rate is from 0.1 milliliters per hour to 1 milliliter per hour.

\* \* \* \* \*